United States Patent [19]

Gray

[11] 4,445,366

[45] May 1, 1984

[54] PRESSURE DIFFERENTIAL GAGE AND A METHOD FOR DETECTING THE PRESENCE OF NONCONDENSIBLE GASES IN A REFRIGERATION SYSTEM

[75] Inventor: Kenneth P. Gray, East Syracuse, N.Y.

[73] Assignee: Carrier Corporation, Syracuse, N.Y.

[21] Appl. No.: 383,899

[22] Filed: Jun. 1, 1982

[51] Int. Cl.³ .............................................. G01N 7/14
[52] U.S. Cl. ................................................... 73/64.2
[58] Field of Search ......................... 73/64.2, 29, 716; 340/626, 611

[56] References Cited

U.S. PATENT DOCUMENTS

| | | | |
|---|---|---|---|
| 2,866,339 | 12/1958 | Rhodes et al. | 73/64.2 |
| 3,504,274 | 1/1963 | Eller et al. | 324/36 |
| 3,544,276 | 5/1967 | Merwitz, Sr. | 23/253 |
| 3,905,237 | 9/1975 | Smalarz et al. | 73/393 |
| 3,926,038 | 12/1975 | Wunning et al. | 73/61.1 R |
| 4,034,597 | 7/1977 | Fredriksson | 73/29 |
| 4,110,998 | 9/1978 | Owen | 62/125 |

FOREIGN PATENT DOCUMENTS 953460  3/1964  United Kingdom ................ 73/64.2

Primary Examiner—Donald O. Woodiel
Attorney, Agent, or Firm—David L. Adour

[57] ABSTRACT

A pressure differential gage and a method for detecting the presence of noncondensible gases in a refrigeration system. The pressure differential gage comprises a housing, a diaphragm, first and second tubes, a reference fluid, and indicator means. The diaphragm separates the housing into first and second chambers. The first tube has one end in fluid communication with the first chamber and a second end open to receive a sample vapor, which determines the pressure in the first chamber. The second tube has one end in fluid communication with the second chamber and a closed second end. The reference fluid is located in the second tube and determines the pressure in the second chamber. The indicator means is actuated by the diaphragm to indicate when the pressure in the first chamber differs from the pressure in the second chamber.

11 Claims, 2 Drawing Figures

4,445,366

PRESSURE DIFFERENTIAL GAGE AND A METHOD FOR DETECTING THE PRESENCE OF NONCONDENSIBLE GASES IN A REFRIGERATION SYSTEM

BACKGROUND OF THE INVENTION

This invention generally relates to a pressure differential gage, and more specifically to a pressure differential gage especially well suited for, and to a method for, detecting the presence of noncondensible gases in a refrigeration system.

As is well known in the refrigeration art, the presence of noncondensible gases or vapors such as air in a refrigeration system in undesirable because such gases reduce the capacity of the refrigeration system and increase the amount of work that must be done by the compressor of the system. For this reason,, refrigeration systems are often monitored or checked for the presence of noncondensible gases. Prior art methods and apparatus for detecting the presence of noncondensible gases in a refrigeration system usually employ the principle that the total vapor pressure at a high pressure region of a refrigeration system is the sum of the partial pressures of the refrigerant vapor and the noncondensible vapors at that region.

These prior art arrangements typically involve measuring both the vapor temperature and the total vapor pressure at a selected high pressure region of a refrigeration system, for example in the compressor discharge line or in the condenser of the system. This measured temperature, of course, is the same as the temperature of the refrigerant vapor at the selected region of the refrigeration system, and knowing this refrigerant vapor temperature, a worker or mechanic can refer to a text or chart to determine the partial pressure of the refrigerant vapor at the selected region. The difference, if any, between this determined partial pressure of the refrigerant vapor and the measured total vapor pressure at the selected region of the refrigeration system indicates the presence and the amount of noncondensible gases in the refrigeration system.

While these prior art methods and apparatus are effective, they are somewhat time consuming, expensive, and cumbersome. In particular, they involve manual inspection of a number of gages, thus requiring costly manual labor. Also, they require reference to a text or chart which may not always be readily available or easily read.

SUMMARY OF THE INVENTION

In view of the above, an object of the present invention is to provide a very simple, economical, and reliable method for, and a pressure differential gage especially well suited for, detecting the presence of noncondensible gases in a refrigeration system.

Another object of this invention is to provide a pressure differential gage which may be easily used to detect the presence of noncondensible gases in a refrigeration system without requiring reference to any text or chart.

A further object of the present invention is to provide a pressure differential gage that may be employed to detect the presence of noncondensible gases in a refrigeration system without requiring visual inspection or monitoring of the gage.

These and other objects are attained with a pressure differential gage comprising a housing, a pressure sensitive diaphragm, first and second tubes, a supply of reference fluid, and indicator means. The housing defines first and second fluid passages; and the diaphragm is secured within and extends across the interior of the housing, and separates the housing interior into a first chamber in fluid communication with the first fluid passage and a second chamber in fluid communication with the second fluid passage.

The first tube is connected to the housing, and has a first end in fluid communication with the first fluid passage and the first chamber of the housing, and a second end open to receive a sample vapor, the pressure of the sample vapor determining the vapor pressure in the first tube and the first chamber of the housing. The second tube is connected to the housing, and has a first end in fluid communication with the second fluid passage and the second chamber of the housing, and a closed second end. The supply of reference fluid is located in the second tube, the vapor pressure of the reference fluid determining the vapor pressure in the second tube and the second chamber of the housing. The indicator means is connected to the housing and is actuated by the diaphragm to indicate when the vapor pressure in the first chamber of the housing differs from the vapor pressure in the second chamber of the housing.

DETAILED DESCRIPTION OF THE PREFERRED EMBODIMENT

Figure 1:
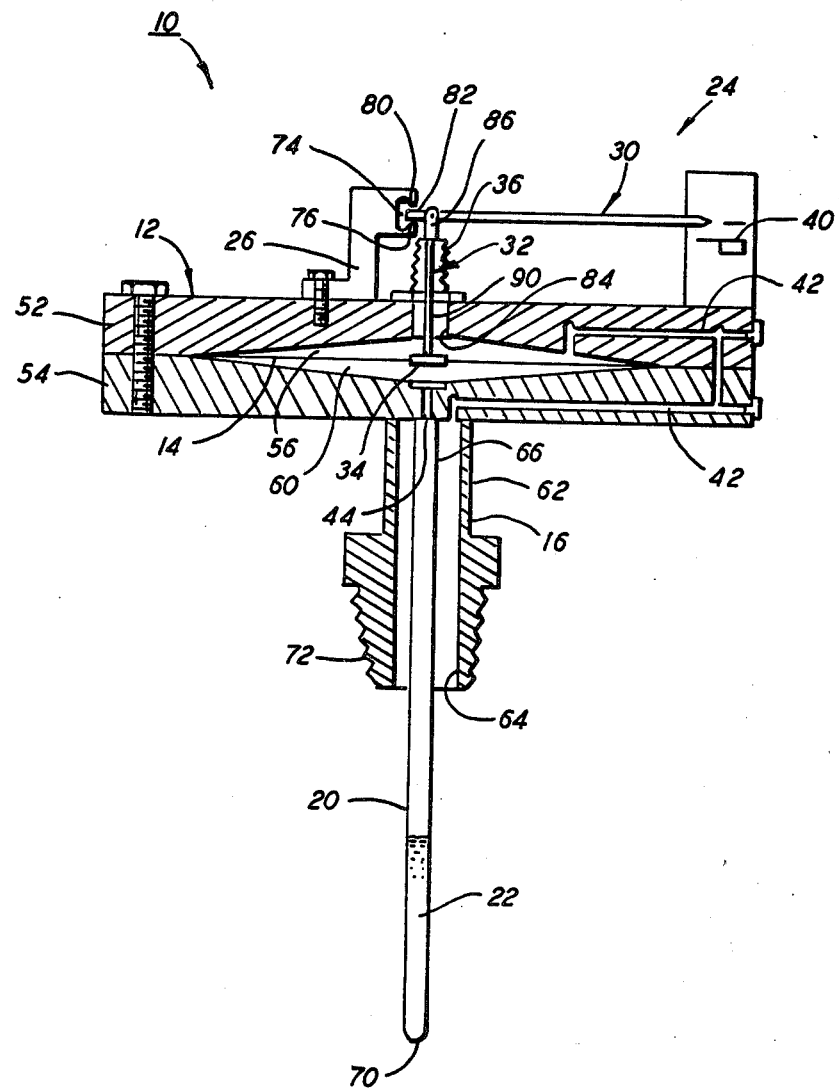
FIG. 1 is a side view partly in cross-section of the preferred embodiment of the pressure differential gage of the present invention.
Figure 2:
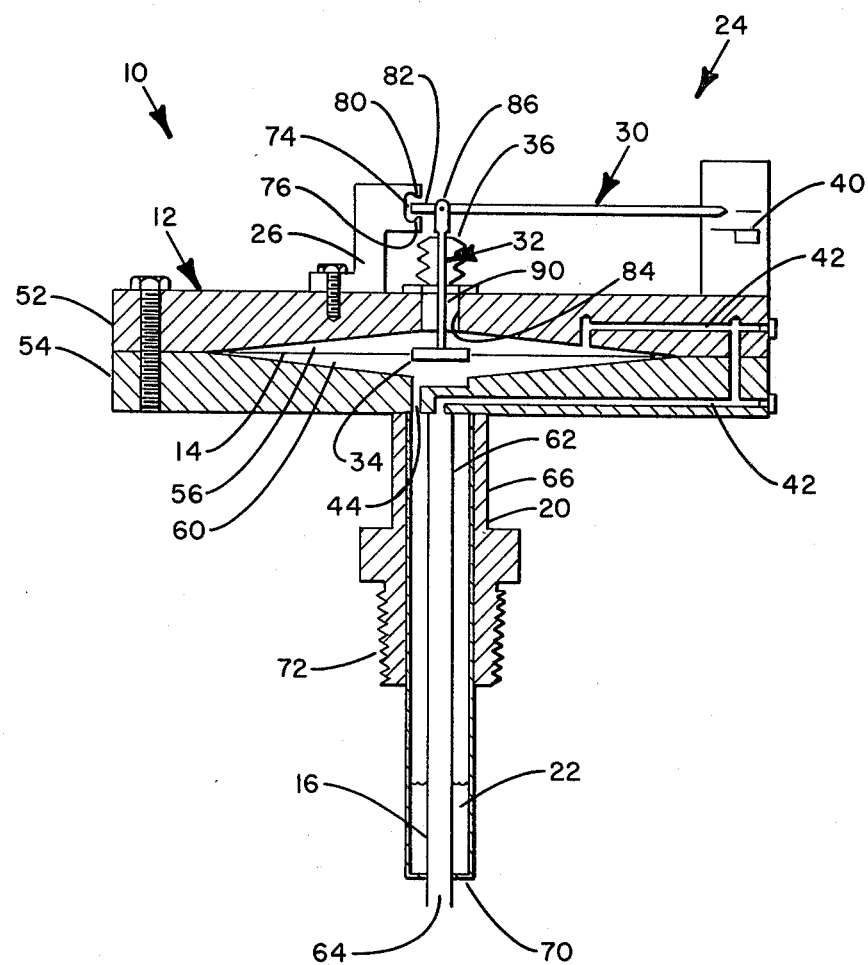
FIG. 2 is a side view partly in cross-section of another embodiment of the pressure differential gage of the present invention.

Referring to FIGS. 1 and 2, wherein like reference numerals identify like elements, there is shown pressure differential gage 10 illustrating teachings of the present invention. Generally, gage 10 comprises housing 12, pressure sensitive diaphragm 14, first tube 16, second tube 20, a supply of reference fluid 22, and indicator means generally referenced as 24. Preferably, indicator means 24 includes fulcrum 26, lever 30, link 32, plate 34, bellows 36, and switch 40.

Housing 12 defines a substantially enclosed interior region or space and first and second fluid passages 42 and 44 for conducting fluid between the interior and the exterior of the housing. As illustrated in the drawing, housing 12 has a substantially closed, cylindrical shape and is formed from two similar upper and lower half sections 52 and 54 that in assembly are secured together by means such as screws or bolts. Upper and lower sections 52 and 54 cooperate to define first fluid passage 42, which extends from a lower outside surface of housing 12, through the lower and upper housing half sections, to an upper portion of the interior of the housing. Lower housing section 54 defines second fluid passage 44, which extends from the lower outside surface of housing 12 to a lower portion of the interior of the housing.

Diaphragm 14 is secured within and extends across the interior of housing 12, and separates the interior thereof into upper chamber 56 in fluid communication with first fluid passage 42 and lower chamber 60 in fluid communication with second fluid passage 44. Preferably, diaphragm 14 extends completely across the interior of housing 12 and peripheral portions of the diaphragm extend between opposed surfaces of half sections 52 and 54 of the housing in a vapor tight, pressure fit against these opposed surfaces. In this way, diaphragm 14 prevents vapor flow between housing chambers 56 and 60 and seals the interface between housing sections 52 and 54. Diaphragm 14 may be held in place simply by the pressure engagement between the peripheral portions of the diaphragm and contiguous surfaces of housing sections 52 and 54. Alternately, specific fastening means such as bolts or pins may be used to secure diaphragm 14 in place.

As shown in FIG. 1, first tube 16 is connected to housing 12, and has first end 62 in fluid communication with first fluid passage 42 and first housing chamber 56, and second end 64 open to receive a sample vapor, wherein the pressure of that sample vapor determines the vapor pressure in the first tube, the first housing chamber, and thus on a first or top face of diaphragm 14. Second tube 20 is also connected to housing 12, and has first end 66 in communication with second fluid passage 44 and second housing chamber 60, and closed second end 70. Reference fluid supply 22 is located in second tube 20, wherein the vapor pressure of the reference fluid determines the vapor pressure in the second tube, in second housing chamber 60, and consequently on a second or bottom face of diaphragm 14.

The specific fluid that is used as reference fluid 22 depends on the particular application of gage 10. For example, if gage 10 is used to detect the presence of noncondensible gases in a system such as a refrigeration system, a fluid having the same pressure-to-temperature relationship as the refrigerant in that system is used as reference fluid 22, and preferably the reference fluid is the same as that refrigerant fluid. In order to insure that reference fluid 22 determines the vapor pressure in second tube 20 and second housing chamber 60, tube 20 may be evacuated of other fluids such as air before or after the preferred reference fluid is placed therein. This may be done by initially providing second tube 20 with an open second end 70, substantially exhausting the gases, vapors and other fluids from the tube via this open second end, placing reference fluid 22 in tube 20, and then pinching and welding the second end of second tube 20 closed.

Various types of tubes 16 and 20 may be employed in the practice of the present invention and these tubes may be connected to housing 12 in a variety of ways. For example, tubes 16 and 20 may be formed from a metal such as copper, first ends 62 and 66 of the tubes may encircle the openings of first and second fluid passages 42 and 44 respectively, and the tubes may be welded to housing 12, specifically bottom section 54 thereof, with the welds extending completely around the circumference of the tubes to form a circumferential seal between these tubes and the housing.

With the embodiment of gage 10 illustrated in FIG. 1, second tube 20 extends through the interior of first tube 16, with the longitudinal axes of these tubes parallel and preferably co-axial. This arrangement is of utility because it is very compact and easy to handle. In particular, only a single, relatively small opening is needed in a housing, body, or shell in order to extend both tubes 16 and 20 into the interior of that housing or body. Also, with this preferred arrangement, connecting fitting 72 is secured to and extends around a lower portion of first tube 16 for connecting gage 10 to an external body, for instance via a plurality of external threads defined by the connecting fitting. Fitting 72 may be integral with first tube 16, or the connecting fitting may be secured to the first tube by welding, with the weld completely extending around the circumference of the first tube to form a seal between that tube and the connecting fitting. It should be pointed out that, with modifications well within the purview of those skilled in the art, instead of the specific arrangement shown in FIG. 1, gage 10 may be constructed with first tube 16 extending through the interior of second tube 20 and with connecting fitting 72 extending around and secured to the second tube, as shown in FIG. 2.

Indicator means 24 is connected to housing 12 and is actuated by diaphragm 14 to indicate when the vapor pressure in first housing chamber 56 differs from the vapor pressure in second housing chamber 60. Discussing indicator means 24 in greater detail, fulcrum 26 is secured to and extends outside housing 12. More specifically, fulcrum 26 is secured, for example by a bolt or a screw, to a top outside surface of top housing section 52 and extends upward therefrom, and the fulcrum defines recess 74 and two opposed, spaced shoulders 76 and 80 extending across the inlet of this recess. Lever 30 is pivotally supported by fulcrum 26. In particular, first end 82 of lever 30 extends into recess 74 and loosely rests on and is thus pivotally supported by fulcrum shoulder 76. Fulcrum shoulder 80 is located above and is slightly spaced from lever 30, loosely capturing first end 82 of lever 30 in recess 74.

At the same time, link 32 is connected to lever 30 and extends into the interior of housing 12 adjacent diaphragm 14. More particularly, housing 12 defines link aperture 84, a first end of link 32 is pivotally connected to first end 82 of lever 30, for instance by a pin extending through aligned openings defined by the first ends of the link and the lever, and the link extends through link aperture 84 into the interior of the housing. Plate 34 is connected to link 32 adjacent diaphragm 14, and preferably the plate is secured to a second end of the link and to a central portion of the diaphragm for unitary movement with both the link and this central portion of the diaphragm.

It is desirable to provide means for inhibiting or preventing vapor flow out of the interior of housing 12 through link aperture 84, and in the embodiment of gage 10 depicted in the drawing, this means takes the form of bellows 36. Bellows 36 is secured to top section 52 of housing 12 and completely encircles and covers the top of link aperture 84. With this preferred embodiment, it should be noted, link 32 comprises first section 86 connected to both lever 30 and the outside of a top surface of bellows 36, and second section 90 connected to the inside of the top surface of the bellows and extending therefrom, through link aperture 84, and into the interior of housing 12. In addition, the surface area of the top of bellows 36 is substantially less than the surface area of diaphragm 14 so that the pressure forces acting on the top of the bellows is minimal compared to the pressure forces acting on the diaphragm.

With the above-described indicator means 24, if the vapor pressure in first housing chamber 56 exceeds the vapor pressure in second housing chamber 60, then this vapor pressure differential forces the central portion of diaphragm 14 to flex downward within housing 12. Diaphragm 14 engages and moves plate 34 downward, and this pulls link 32 downward. This pivots lever 30 generally about fulcrum shoulder 76, and in particular pivots the second end of the lever downward. When the pressure difference between first and second housing chambers 56 and 60 reaches a predetermined value, diaphragm 14, specifically the central portion thereof, reaches a predetermined position within housing 12 and lever 30 pivots to a preset position. This, by itself, may be employed as a signal to indicate that the pressure in first chamber 56 exceeds the pressure in second chamber 60 by a preset amount.

Preferably, though, switch 40 is located so that lever 30 actuates the switch when the lever reaches the above-identified preset position. Switch 40, in turn, may be used to activate a light, bulb, or buzzer to bring to the attention of a worker or attendant the fact that the predetermined pressure differential between first and second housing chambers 56 and 60 has been reached. Of course, with the particular embodiment discussed above, not only will lever 30 indicate when the pressure differential between first and second housing chambers 56 and 60 reaches a predetermined value, but since plate 34 and lever 30 continuously move with diaphragm 14, the lever also continuously indicates the position of the diaphragm and continuously indicates the pressure difference between first and second chambers 56 and 60.

Gage 10 is especially well-suited for detecting the presence of noncondensible gases in a refrigeration system. To do this, both tubes 16 and 20 are inserted into a high pressure vapor side of the refrigeration system. This may be done, as an example, by providing the condenser housing or shell of the system with a small opening and inserting the second ends of both tubes 16 and 20 through this opening into the interior of the condenser. With tubes 16 and 20 so inserted, gage 10 may be secured to the condenser housing or shell via connecting fitting 72. Preferably, it should be pointed out, gage 10 is so connected to the refrigeration system while that system is being assembled, and the gage remains connected to the refrigeration system during the operation thereof, providing a continuous monitoring of the noncondensible gases in this system. Also, it is desirable to solder fitting 22 to the condenser housing or shell to prevent vapor from leaking through the interface therebetween.

Referring to FIG. 1, when the refrigeration system operates, with the second, open end 64 of first tube 16 inserted into the high pressure vapor side of the refrigeration system, vapor therefrom is conducted through the first tube, through first fluid passage 42 and into first housing chamber 56, bringing the vapor pressure therein and the vapor pressure on the first side of diaphragm 14 to the same as the total vapor pressure (that is, the sum of the partial pressure of the refrigerant vapor plus the partial pressure of any noncondensible vapors mixed therein) in the high pressure vapor side of the refrigeration system. At the same time, with second end 70 of second tube 20 inserted into the high pressure vapor side of the refrigeration system, the natural conduction of heat between the vapor at this location of the refrigeration system and the reference fluid 22 in the second tube brings the temperature of that reference fluid to the temperature of the vapor in the high pressure vapor side of the refrigeration system, which of course is the same temperature as that of the refrigerant vapor at that location in the refrigeration system. This is true, it may be noted, even though tube 20 maintains reference fluid 22 physically separated from the vapor in the refrigeration system.

Since reference fluid 22 has the same pressure-to-temperature relationship as the refrigerant fluid used in the refrigeration system, bringing the temperature of the reference fluid to the temperature of the refrigerant vapor in the high pressure vapor side of the refrigeration system, brings the pressure of the reference fluid to the partial pressure of that refrigerant vapor. This, then, brings the vapor pressure in second housing chamber 60 and the vapor pressure against the second surface or face of diaphragm 14 to the same pressure as the partial pressure of the refrigerant vapor in the high pressure vapor side of the refrigeration system.

Diaphragm 14, as explained above, senses the difference between the pressures in first and second chambers 56 and 60. Hence, when gage 10 is employed as described immediately above, the diaphragm senses the difference between the partial pressure of the refrigerant vapor at the high pressure vapor side of the refrigeration system and the total vapor pressure at that location. This pressure difference, if it exists, is due to the presence of noncondensible vapors in the refrigeration system. When the partial pressure of these noncondensible contaminents reaches a preset value, the above-mentioned pressure difference reaches a preset value; and, also as explained above, when this occurs, diaphragm 14 reaches the preset position to actuate indicator means 24.

While it is apparent that the invention herein disclosed is well calculated to fulfill the objects stated above, it will be appreciated that numerous modifications and embodiments may be devised by those skilled in the art, and it is intended that the appended claims cover all such modifications and embodiments as fall within the true spirit and scope of the present invention.

I claim:

1. A pressure differential gage comprising:

a housing defining first and second fluid passages;

a pressure sensitive diaphragm secured within and extending across the interior of the housing, and separating the housing interior into a first chamber in fluid communication with the first fluid passage and a second chamber in fluid communication with the second fluid passage;

a first tube connected to the housing, and having a first end in fluid communication with the first fluid passage and the first chamber of the housing, and a second end open to receive a sample vapor, the pressure of the sample vapor determining the vapor pressure in the first tube and the first chamber of the housing;

a connecting fitting secured to the first tube for connecting the pressure differential gage to an external body;

a second tube connected to the housing and extending through the first tube, and having a first end in fluid communication with the second fluid passage and the second chamber of the housing, and a closed second end;

a supply of reference fluid located in the second tube, the vapor pressure of the reference fluid determining the vapor pressure in the second tube and the second chamber of the housing; and indicator means connected to the housing and actuated by the diaphragm to indicate when the vapor pressure in the first chamber of the housing differs from the vapor pressure in the second chamber of the housing.

2. The pressure differential gage as defined by claim 1 wherein the indicator means includes:
- a fulcrum secured to an extending outside the housing;
- a lever pivotally supported by the fulcrum;
- a link connected to the lever and extending into the housing adjacent the diaphragm; and
- a plate secured to the link;
- the diaphragm engaging the plate to move the link and pivot the lever to a preset position when the difference between the vapor pressures in the first and second chambers of the housing reaches a preset value.

3. The pressure differential gage as defined by claim 2 wherein the plate is secured to the diaphragm for movement therewith.

4. A pressure differential gage comprising:
- a housing including top and bottom sections and defining first and second fluid passages;
- a diaphragm secured within the housing, extending across the interior thereof, and separating the housing into an upper chamber in fluid communication with the first fluid passage and a lower chamber in fluid communication with the second fluid passage;
- a first tube connected to the bottom section of the housing, having a first end in fluid communication with the first fluid passage and the first chamber of the housing, and having a second end open to receive a sample vapor, the pressure of the sample vapor determining the vapor pressure in the first tube and the first chamber of the housing;
- a connecting fitting secured to the first tube for connecting the pressure differential gage to an external body;
- a second tube extending through the first tube and connected to the bottom section of the housing, having a first end in fluid communication with the second fluid passage and the second chamber of the housing, and having a closed second end;
- a supply of reference fluid located in the second tube, the vapor pressure of the reference fluid determining the vapor pressure in the second tube and the second chamber of the housing;
- a fulcrum secured to the top section of the housing and extending upward therefrom;
- a lever pivotally supported by the fulcrum;
- a link connected to the lever and extending therefrom into the housing adjacent the diaphragm; and
- a plate secured to the link, the diaphragm moving the plate and link downward to pivot the lever to a preset position upon the presence of a difference between the vapor pressures in the upper and lower chambers of the housing.

5. A method for detecting the presence of non-condensible gases in a refrigeration system, comprising the steps of:
- inserting an end of a tube, which has a fluid with the same pressure-to-temperature characteristics as a refrigerant in the refrigeration system, into a high pressure vapor side of the refrigeration system;
- bringing the temperature of the fluid in the tube to the temperature of vapor in the high pressure vapor side of the refrigeration system;
- sensing the difference betwen the pressure of the fluid in the tube and the pressure of the vapor in the high pressure vapor of the refrigeration system; and
- indicating the existence of a sensed pressure difference.

6. A method as defined by claim 5 wherein the inserting step includes the step of maintaining the fluid in the tube separate from the vapor in the high pressure vapor side of the refrigeration system.

7. A method as defined by claim 6 wherein:
- the sensing step includes the steps of
- bringing the pressure on a first side of a diaphragm to the same pressure as the vapor in the high pressure vapor side of the refrigeration system; and
- bringing the pressure on a second side of the diaphragm to the same pressure as the fluid in the tube; and
- the indicating step includes the step of indicating when the diaphragm reaches a preset position.

8. A pressure differential gage comprising:
- a housing defining first and second fluid passages;
- a pressure sensitive diaphragm secured within and extending across the interior of the housing, and separating the housing interior into a first chamber in fluid communication with the first fluid passage and a second chamber in fluid communication with the second fluid passage;
- a first tube connected to the housing, and having a first and in fluid communication with the first fluid passage and the first chamber of the housing, and a second end open to receive a sample vapor, the pressure of the sample vapor determining the vapor pressure in the first tube and the first chamber of the housing;
- a second tube connected to the housing, with the first tube extending through the second tube, said second tube having a first end in fluid communication with the second fluid passage and the second chamber of the housing, and a closed second end;
- a connecting fitting secured to the second tube for connecting the pressure differential gage to an external body;
- a supply of reference fluid located in the second tube, the vapor pressure of the reference fluid determining the vapor pressure in the second tube and the second chamber of the housing; and
- indicator means connected to the housing and actuated by the diaphragm to indicate when the vapor pressure in the first chamber of the housing differs from the vapor pressure in the second chamber of the housing.

9. The pressure differential gage is defined by claim 8 wherein the indicator means includes:
- a fulcrum secured to and extending outside the housing;
- a lever pivotally supported by the fulcrum;
- a link connected to the lever and extending into the housing adjacent to diaphragm; and
- a plate secured to the link;
- the diaphragm engaging the plate to move the link and pivot the lever to a preset position when the difference between the vapor pressures in the first and second chambers of the housing reaches a preset value.

10. The pressure differential gage as defined by claim 9 wherein the plate is secured to the diaphragm for movement therewith.

11. A pressure differential gage comprising:
- a housing including top and bottom sections and defining first and second fluid passages;
- a diaphragm secured within the housing, extending across the interior thereof, and separating the housing into an upper chamber in fluid communication with the first fluid passage and a lower chamber in fluid communication with the second fluid passage;

a first tube connected to the bottom section of the housing, having a first end in fluid communication with the first fluid passage and the first chamber of the housing, and having a second end open to receive a sample vapor, the pressure of the sample vapor determining the vapor pressure in the first tube and the first chamber of the housing;

a second tube connected to the bottom section of the housing, with the first tube extending through the second tube, the second tube having a first end in fluid communication with the second fluid passage and the second chamber of the housing, and having a closed second end;

a connecting fitting secured to the second tube for connecting the pressure differential gage to an external body;

a supply of reference fluid located in the second tube, the vapor pressure of the reference fluid determining the vapor pressure in the second tube and the second chamber of the housing;

a fulcrum secured to the top section of the housing and extending upward therefrom;

a lever pivotally supported by the fulcrum;

a link connected to the lever and extending therefrom into the housing adjacent the diaphragm; and a plate secured to the link, the diaphragm moving the plate and link downward to pivot the lever to a preset position upon the presence of a difference between the vapor pressures in the upper and lower chambers of the housing.

* * * * *